(12) United States Patent
Ferree et al.

(10) Patent No.: US 7,060,100 B2
(45) Date of Patent: Jun. 13, 2006

(54) ARTIFICIAL DISC AND JOINT REPLACEMENTS WITH MODULAR CUSHIONING COMPONENTS

(76) Inventors: Bret A. Ferree, 1238 Cliff Laine Dr., Cincinnati, OH (US) 45208; David Tompkins, 647 Wallace Ave., Milford, OH (US) 45150

( * ) Notice: Subject to any disclaimer, the term of this patent is extended or adjusted under 35 U.S.C. 154(b) by 0 days.

(21) Appl. No.: 10/892,795

(22) Filed: Jul. 16, 2004

(65) Prior Publication Data

US 2004/0260396 A1 Dec. 23, 2004

Related U.S. Application Data

(63) Continuation-in-part of application No. 10/303,385, filed on Nov. 25, 2002, which is a continuation-in-part of application No. 10/191,639, filed on Jul. 9, 2002, which is a continuation-in-part of application No. 09/415,382, filed on Oct. 8, 1999, now Pat. No. 6,419,704, and a continuation-in-part of application No. 09/580,231, filed on May 26, 2000, now Pat. No. 6,494,883.

(51) Int. Cl.
*A61F 2/44* (2006.01)
(52) U.S. Cl. .................................. 623/17.16
(58) Field of Classification Search .. 623/17.11–17.16, 623/20.32–20.34
See application file for complete search history.

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,657,550 A | 4/1987 | Daher | 606/61 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A | 9/1988 | Ray et al. | 623/17.11 |
| 4,863,477 A | 9/1989 | Monson | 623/17.11 |
| 4,874,389 A | 10/1989 | Downey | 623/17 |
| 4,878,915 A | 11/1989 | Brantigan | 623/17 |
| 4,904,260 A | 2/1990 | Ray et al. | 623/17.16 |
| 4,911,718 A | 3/1990 | Lee et al. | 623/17 |

(Continued)

*Primary Examiner*—Suzette J-J Gherbi
(74) *Attorney, Agent, or Firm*—Gifford, Krass, Groh, Sprinkle, Anderson & Citkowski, PC (57) ABSTRACT

An artificial joint or disc replacement (ADR) broadly includes a pair of opposing endplate components, each attached to one of the upper and lower vertebrae, a cushioning component disposed between the endplate components, and a mechanism for coupling the cushioning component to one or both of the endplates. In the preferred embodiment, the cushioning component takes the form of a tire-like outer structure attached to an inner hub. A filler material is also preferably contained within the cushioning component. The filler material may be a gas, liquid, foam, or gel, including a hydrogel. One or both of the endplate components may include a modified surface to increase adherence to respective opposing bone surfaces.

11 Claims, 9 Drawing Sheets

U.S. PATENT DOCUMENTS

| | | | | |
|---|---|---|---|---|
| 4,917,704 | A | 4/1990 | Frey et al. | 623/17 |
| 4,932,969 | A | 6/1990 | Frey et al. | 623/17 |
| 4,946,378 | A | 8/1990 | Hirayama et al. | 623/17 |
| 5,002,576 | A | 3/1991 | Fuhrmann et al. | 623/17 |
| 5,026,373 | A | 6/1991 | Ray et al. | 606/61 |
| 5,035,716 | A | 7/1991 | Downey | 623/17 |
| 5,047,055 | A * | 9/1991 | Bao et al. | 623/17.16 |
| 5,071,437 | A * | 12/1991 | Steffee | 623/17.16 |
| 5,108,438 | A | 4/1992 | Stone | 623/17 |
| 5,123,926 | A | 6/1992 | Pisharodi | 623/17 |
| 5,171,280 | A | 12/1992 | Baumgartner | 623/17 |
| 5,171,281 | A | 12/1992 | Parsons et al. | 623/17 |
| 5,192,326 | A | 3/1993 | Bao et al. | 606/60 |
| 5,192,327 | A | 3/1993 | Brantigan | 606/60 |
| 5,245,773 | A | 9/1993 | Snyder | 623/17 |
| 5,246,458 | A | 9/1993 | Graham | 623/17 |
| 5,258,031 | A | 11/1993 | Salib et al. | 623/17 |
| 5,258,043 | A | 11/1993 | Stone | 623/66 |
| 5,292,332 | A | 3/1994 | Lee | 606/213 |
| 5,314,477 | A | 5/1994 | Marnay | 623/17 |
| 5,320,644 | A | 6/1994 | Baumgartner | 623/17 |
| 5,336,223 | A | 8/1994 | Rogers | 606/61 |
| 5,370,697 | A | 12/1994 | Baumgartner | 623/17 |
| 5,375,823 | A | 12/1994 | Navas | 267/195 |
| 5,401,269 | A | 3/1995 | Buttner-Janz et al. | 623/17 |
| 5,458,642 | A | 10/1995 | Beer et al. | 623/17 |
| 5,464,421 | A | 11/1995 | Wortrich | 606/213 |
| 5,514,180 | A | 5/1996 | Heggeness et al. | 623/17.11 |
| 5,534,028 | A | 7/1996 | Bao et al. | 623/17 |
| 5,534,030 | A | 7/1996 | Navarro et al. | 623/17 |
| 5,545,229 | A | 8/1996 | Parsons et al. | 623/17 |
| 5,556,431 | A | 9/1996 | Buttner-Janz | 623/17 |
| 5,571,192 | A | 11/1996 | Schonhoffer | 606/61 |
| 5,609,635 | A | 3/1997 | Michelson | 623/17 |
| 5,645,565 | A | 7/1997 | Rudd et al. | 606/213 |
| 5,645,596 | A | 7/1997 | Kim et al. | 623/17 |
| 5,645,597 | A | 7/1997 | Krapiva | 623/17 |
| 5,674,294 | A | 10/1997 | Bainville et al. | 623/17 |
| 5,674,296 | A | 10/1997 | Bryan et al. | 623/17 |
| 5,683,465 | A | 11/1997 | Shinn et al. | 623/17 |
| 5,693,100 | A | 12/1997 | Pisharodi | 623/17.16 |
| 5,702,450 | A | 12/1997 | Bisserie | 623/17 |
| 5,702,455 | A | 12/1997 | Saggar | 623/17.15 |
| 5,711,960 | A | 1/1998 | Shikinami | 424/426 |
| 5,716,416 | A | 2/1998 | Lin | 623/17 |
| 5,800,549 | A | 9/1998 | Bao et al. | 623/17 |
| 5,814,084 | A | 9/1998 | Grivas et al. | 623/23.48 |
| 5,824,093 | A | 10/1998 | Ray et al. | 623/17 |
| 5,824,094 | A | 10/1998 | Serhan et al. | 623/17 |
| 5,827,328 | A * | 10/1998 | Buttermann | 623/17.13 |
| 5,865,845 | A | 2/1999 | Thalgott | 623/17 |
| 5,865,846 | A | 2/1999 | Bryan et al. | 623/17 |
| 5,888,226 | A | 3/1999 | Rogozinski | 623/17 |
| 5,893,889 | A | 4/1999 | Harrington | 623/17 |
| 5,899,941 | A | 5/1999 | Nishijima et al. | 623/17 |
| 5,906,616 | A | 5/1999 | Pavlov et al. | 606/61 |
| 5,928,284 | A | 7/1999 | Mehdizadeh | 623/17 |
| 5,964,807 | A | 10/1999 | Gan et al. | 623/17.11 |
| 5,976,186 | A | 11/1999 | Bao et al. | 623/17.16 |
| 6,022,376 | A | 2/2000 | Assell et al. | 623/17.16 |
| 6,045,554 | A | 4/2000 | Grooms et al. | 606/73 |
| 6,090,112 | A | 7/2000 | Zucherman et al. | 606/61 |
| 6,110,210 | A | 8/2000 | Norton et al. | 623/17.16 |
| 6,113,639 | A | 9/2000 | Ray et al. | 623/17.16 |
| 6,132,465 | A | 10/2000 | Ray et al. | 623/17.16 |
| 6,146,420 | A | 11/2000 | McKay | 623/17.11 |
| 6,187,048 | B1 | 2/2001 | Milner et al. | 623/17.12 |
| 6,200,347 | B1 | 3/2001 | Anderson et al. | 623/11.11 |
| 6,214,050 | B1 | 4/2001 | Huene | 623/17.15 |
| 6,245,072 | B1 | 6/2001 | Zdeblick et al. | 606/61 |
| 6,258,126 | B1 * | 7/2001 | Colleran | 623/20.29 |
| 6,261,586 | B1 | 7/2001 | McKay | 424/422 |
| 6,270,528 | B1 | 8/2001 | McKay | 623/16.11 |
| 6,402,785 | B1 * | 6/2002 | Zdeblick et al. | 623/17.16 |
| 6,533,818 | B1 * | 3/2003 | Weber et al. | 623/17.16 |
| 2001/0020186 | A1 | 9/2001 | Boyce et al. | 623/17.16 |
| 2001/0034553 | A1 | 10/2001 | Michelson | 623/17.11 |
| 2001/0039458 | A1 | 11/2001 | Boyer, II et al. | 623/23.63 |
| 2001/0056302 | A1 | 12/2001 | Boyer, II et al. | 623/17.15 |
| 2004/0225361 | A1 * | 11/2004 | Glenn et al. | 623/17.12 |
| 2005/0096744 | A1 * | 5/2005 | Trieu et al. | 623/17.11 |

* cited by examiner

ARTIFICIAL DISC AND JOINT REPLACEMENTS WITH MODULAR CUSHIONING COMPONENTS

REFERENCE TO RELATED APPLICATIONS

This application is a continuation-in-part of U.S. patent application Ser. No. 10/303,385, filed Nov. 25, 2002; which is a continuation-in-part of U.S. patent application Ser. No. 10/191,639, filed Jul. 9, 2002; which is a continuation-in-part of U.S. patent application Ser. No. 09/415,382, filed Oct. 8, 1999, now U.S. Pat. Nos. 6,419,704, and 09/580,231, filed May 26, 2000, now U.S. Pat. No. 6,494,883. The entire content of each application and patent is incorporated herein by reference.

FIELD OF THE INVENTION

This invention relates generally to surgical techniques and prosthetic components therefore and, in particular, to intervertebral disc replacement apparatus and methods of implanting the same.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction).

The annulus contains the nucleus. The nucleus pulpous serves to transmit and dampen axial loads. A high water content (70–80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration.

Generally Disc Degeneration is Painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

SUMMARY OF THE INVENTION

This invention resides in an artificial joint or disc replacement (ADR) configured for placement between upper and lower vertebrae. The implant broadly includes a pair of opposing endplate components, each attached to one of the upper and lower vertebrae, a cushioning component disposed between the endplate components, and a mechanism for coupling the cushioning component to one or both of the endplates.

In the preferred embodiment, the cushioning component takes the form of a tire-like outer structure attached to an inner hub. A filler material is also preferably contained within the cushioning component. The filler material may be a gas, liquid, foam, or gel, including a hydrogel. If a solid, foam, gel or hydrogel is used, such material may be used as a single piece or as multiple pieces.

One or both of the endplate components may include a modified surface to increase adherence to the respective vertebral endplates or opposing bone surfaces in the case of a joint replacement. Such surface modification may include spikes, barbs or other projections, and/or pores or roughening conducive to bony ingrowth.

DETAILED DESCRIPTION OF THE DRAWINGS

U.S. Pat. No. 6,419,704 discloses artificial replacements for natural intervertebral discs in humans and animals. Broadly, a shaped body assumes a final volume sized to consume at least a portion of the intervertebral disc space, and a material associated with the shaped body enabling the body to cyclically compress and expand in a manner similar to the disc material being replaced. The body may be composed of a compressible material, such as polymeric urethane or other suitable elastomers, or may include a filling to impart an appropriate level of compressibility. The superior and inferior surfaces may be convex, and may further include grooves, spikes, or other protrusions to maintain the body within the intervertebral space. The body may further be wedge-shaped to help restore or maintain lordosis, particularly if the prosthesis is introduced into the cervical or lumbar regions of the spine.

To enhance strength or longevity, the body may further include the use of fiber-reinforced materials on one or more outer surfaces or wall structures, as the case may be. Similar to commercial tire construction, such fiber-reinforced materials may be of a bias-ply, radial-ply or bias-belted construction. According to one configuration, an artificial disc according to the invention may further include an outer compressible member peripherally attached to a central "hub," similar, at least in concept, to the which a tire is mounted onto a wheel.

The instant invention extends the teachings of the '704 patent through the addition of metal endplates, bone-ingrowth surfaces, and/or modular, interlocking components. Although the invention is described in terms of artificial disc replacement (ADR), the approach may also be used to dampen other artificial joints within the body, such as the tibial component of a knee replacement.

As noted in the '704 patent, the ADR may be filled with a gas, liquid, gel (including hydrogels), foam or other compressible material, and the material may be introduced or otherwise provided through the use of a valve, port, syringe, or, alternatively, by way of valveless means. The body in this case is preferably a sealed unit, and may include self-sealing means in the event of a leak or rupture.

If a valve is used to inflate the ADR, it may be configured so as to be accessible during implantation, enabling the surgeon to expand the device in situ. A valve may also be provided in the form of a port enabling subcutaneous post-operative inflation or re-expansion. If a hydrogel is used as the filler material, it may introduced within the body in a dehydrated state prior to implantation, with water being added to expand the material. The liquid may be added through a valve, port or hypodermic in conjunction within a sealed structure or, alternatively, at least a portion of the surface of the body, preferably the superior end or inferior surfaces, may be at least semi-porous. As a further alternative to a valveless structure, one or more reactants may be provided with the body, such that when mixed with one or more other reactants, a gas or foam is generated to expand and fill the body. As yet a further alternative, an ampule or cartridge operative to release a compressed gas or generate a gas, liquid or foam may be activated by an external source of energy such as ultrasound, heat, or other stimuli.

Figures 1, 2:
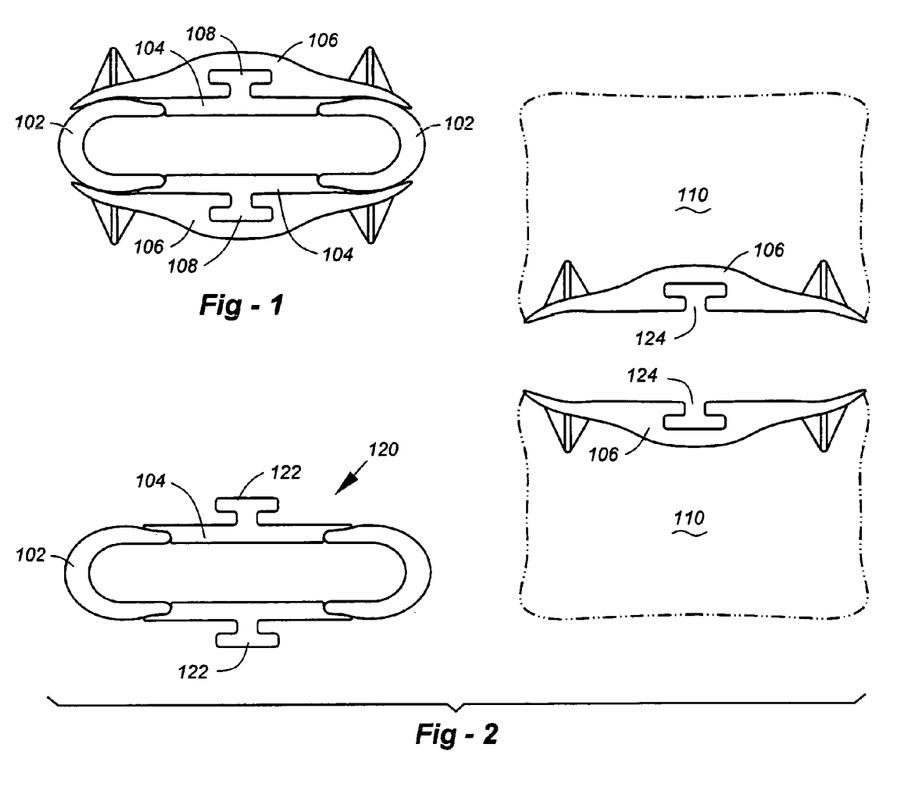
FIG. 1 is a sagittal cross section of an ADR (artificial disc replacement) according to the invention.
FIG. 2 is a view of the anterior aspect of the spine with the ADR endplates attached to the vertebrae.

Turning now to the figures, FIG. 1 is a sagittal cross section of an embodiment of an ADR according to this invention, including a tire-like component 102, hub-like component 104, and endplates 106.

FIG. 2 is a view of the anterior aspect of the spine with the ADR endplates attached to the vertebrae 110. A sagittal cross section of the modular compressible member is also illustrated at 120. The ends of the hub have projections 122 that slide into grooves 124 on the ADR endplates.

Figure 3:
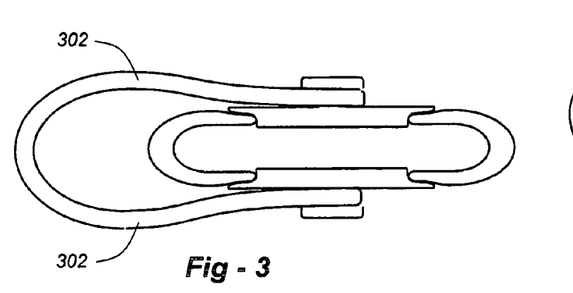
FIG. 3 shows a removable device such as a clip used to hold the hub-like components to the tire-like components until the compressible component is inserted into the ADR endplates.

FIG. 3 shows how a removable device such as a clip 302 can be used to hold the hub-like components to the tire-like components until the compressible component is inserted into the ADR endplates. The clip 302 is especially important when the compressible component contains hydrated hydrogel. In such embodiments, the hydrogel may be stored in fluid to allow the component to be inserted with the hydrogel fully hydrated or nearly fully hydrated. The hydrogel-containing embodiments further include pores for fluid transport through the ADR endplates, the hub-like component, and/or the tire-like component.

Figure 4:
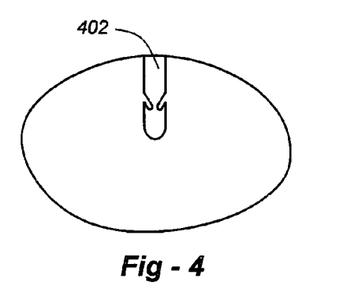
FIG. 4 is an axial cross section through one embodiment of the ADR endplate.

FIG. 4 is an axial cross section through one embodiment of an ADR endplate according to the invention including a recess 402 from the side of the endplate configured to trap the projection 122 from the hub-like component.

Figure 5A:
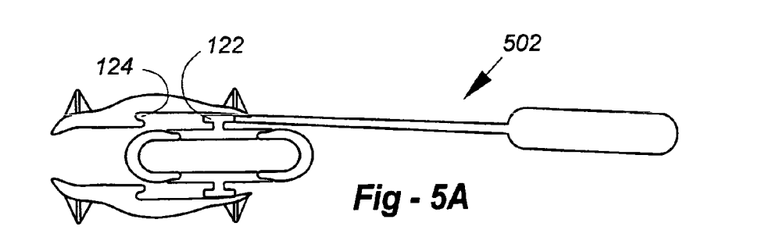
FIG. 5A is a sagittal cross section of a modular ADR during assembly.
Figure 5B:
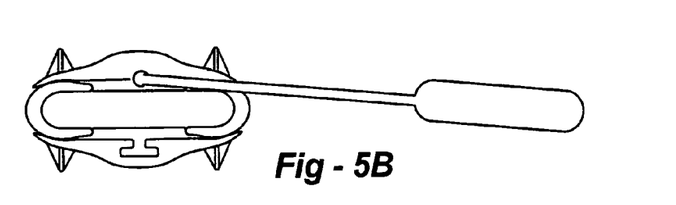
FIG. 5B is a sagittal cross section of the front of the ADR of FIG. 5A with a tool positioned over the projection from the hub.

FIG. 5A is a sagittal cross section of the ADR during assembly of the modular components. A tool 502 is used to push the projections 122 from the hub-like components into the grooves 124 of the ADR endplates, thus forcing the compressible component between the ADR endplates. FIG. 5B is a sagittal cross section of the front of the ADR drawn in FIG. 5A with the tool positioned over the projection from the hub.

Figure 6:
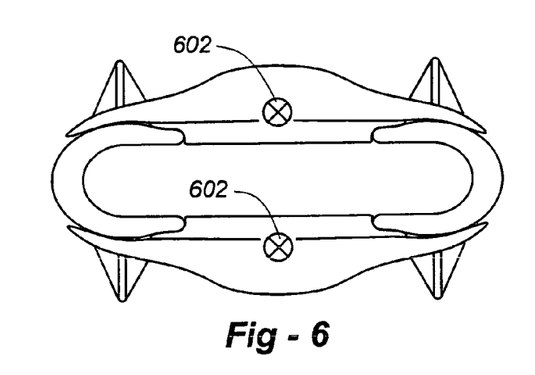
FIG. 6 is a sagittal cross section of the front of the ADR with an alternative mechanism to hold the modular compressible component between the ADR endplates.

FIG. 6 is a sagittal cross section of the front of the ADR with an alternative mechanism used to hold the modular compressible component between the ADR endplates. In this embodiment, screws 602 are threaded into the ADR endplates after insertion of the compressible component. Hub projections and ADR endplate grooves similar to those drawn in FIG. 2 can be used with the screws 602. Mechanisms to prevent screw back-out, such those used in plates associated with the cervical spine, can be incorporated into the endplate(s).

Figure 7A:
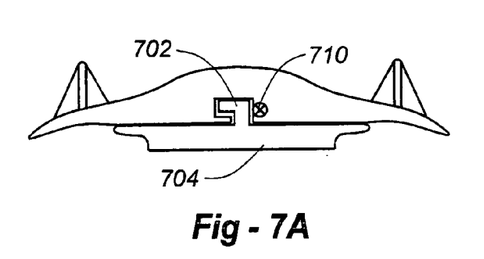
FIG. 7A is a sagittal cross section of another mechanism to connect the hubs to the ADR endplates.
Figure 7B:
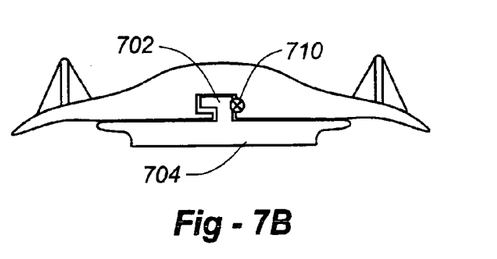
FIG. 7B is a sagittal cross section of the locking mechanism of FIG. 7A with the cam in the locked position.

FIG. 7A is a sagittal cross section of yet a different mechanism used to connect the hubs to the ADR endplates. An L-shaped projection 702 from the hub 704 slides into a corresponding groove in the ADR endplate. A cam lock 710 may be used to hold the components together. In FIG. 7A, the cam is drawn in the unlocked position. FIG. 7B shows the cam in the locked position.

Figure 8:
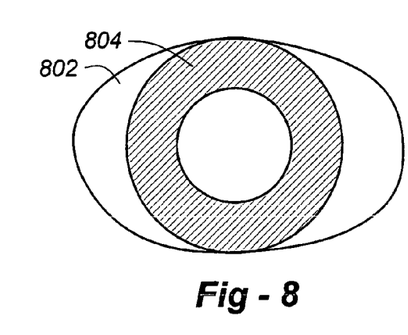
FIG. 8 is a view of the bottom of the top ADR endplate with a circular cushioning component.
Figure 9:
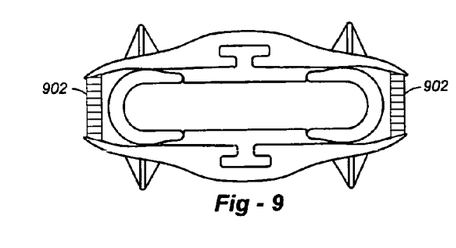
FIG. 9 is a sagittal cross section of the ADR with distraction tools.
Figure 10:
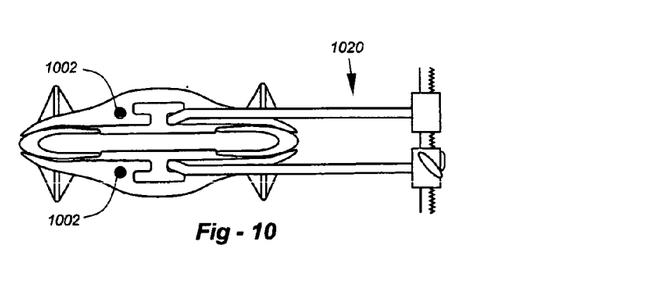
FIG. 10 is a sagittal cross section of the ADR with an alternative distraction mechanism.

FIG. 8 is a view of the bottom of the top ADR endplate 802 with a circular cushioning component 804. The cushioning component can also be circular like the ADR endplate (FIG. 22A), or both can be elliptical (FIG. 22B), or other alternative shape. FIG. 9 is a sagittal cross section of the ADR with distraction tools 902 fitted in the area of the eclipse shaped ADR endplates that is not covered by the circularly shaped cushioning component 804. FIG. 10 is a sagittal cross section of an ADR with an alternative distraction mechanism incorporating endplates with holes 1002 for the arms of a distraction device 1020 placed into the holes on the right side of the ADR.

Figure 11A:
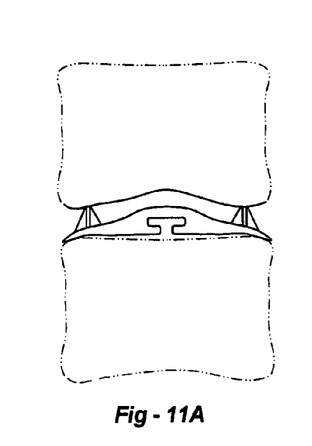
FIG. 11A is the first of a series of drawings showing insertion of the ADR from the anterior aspect of the spine.
Figure 11B:
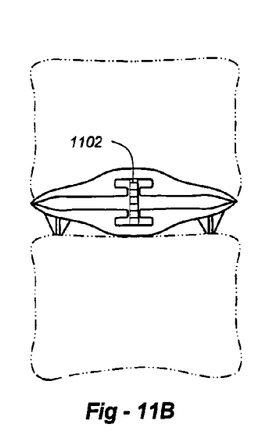
FIG. 11B shows the next step in the insertion of the ADR after FIG. 11A. The bottom ADR endplate is shown during insertion into the inferior vertebra.

FIG. 11A is the first of a series of drawings showing insertion of the ADR from the anterior aspect of the spine. In this Figure, the top ADR endplate is forced into the superior vertebra. The endplate of the vertebra may be milled to improve the fit between the ADR endplate and the vertebra. FIG. 11B is a view of the next step in the insertion of the ADR after FIG. 11A. The bottom ADR endplate is shown during insertion into the inferior vertebra. A tool 1102 may be used to align the ADR endplates. The tool can also be wedge-shaped to help force the ADR endplates into the vertebrae as the tool is forced between the ADR endplates.

Figure 11C:
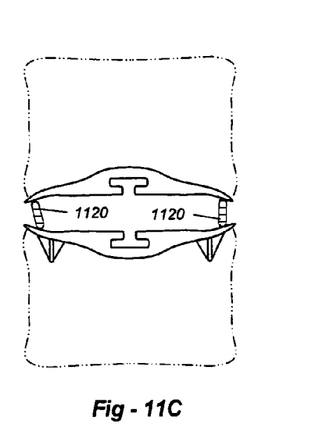
FIG. 11C shows the next step in the insertion of the ADR after FIG. 11B. Distraction tools are used to increase the space between the ADR endplates.

FIG. 11C is a view of the next step in the insertion of the ADR after FIG. 11B. Distraction tools 1120 are used to increase the space between the ADR endplates. The tools can be twisted to cam open the disc space, as illustrated on the left side of the drawing. Alternatively, the distraction tools can be wedge-shaped to force the ADR endplates apart as the wedge shaped tools are driven between them.

Figure 11D:
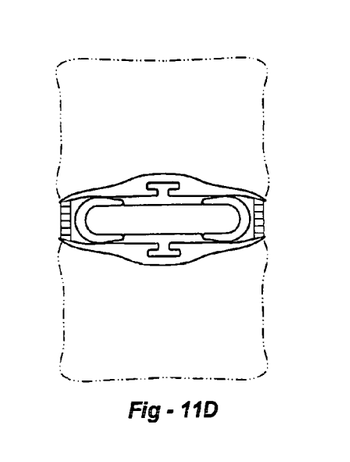
FIG. 11D shows the next step in the insertion of the ADR after FIG. 11C. The cushioning module is positioned between the ADR endplates.
Figure 11E:
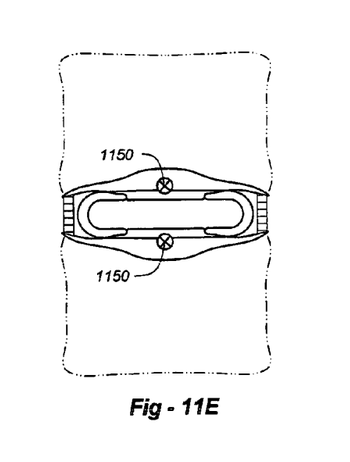
FIG. 11E shows next step in the insertion of the ADR after FIG. 11D. The distraction tools have been removed.

FIG. 11D is a view of the next step in the insertion of the ADR after FIG. 11C, with the cushioning module positioned between the ADR endplates. FIG. 11E is a view of the next step in the insertion of the ADR after FIG. 11D. The distraction tools have been removed, and locking screws 1150 have been inserted into the ADR endplates.

Figure 12A:
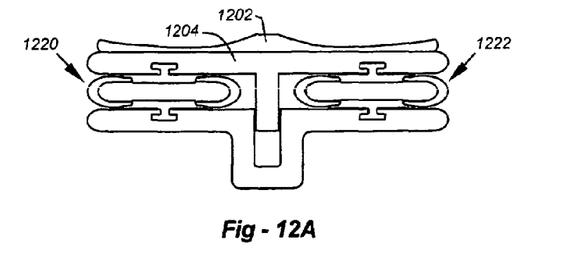
FIG. 12A is a sagittal cross section of an embodiment of the device for cushioning the tibial component of a Total Knee Replacement (TKR)
Figure 12B:
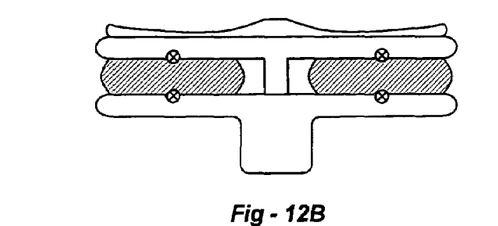
FIG. 12B depicts the front of the tibial component of FIG. 12A.
Figures 12C, 12D, 15:
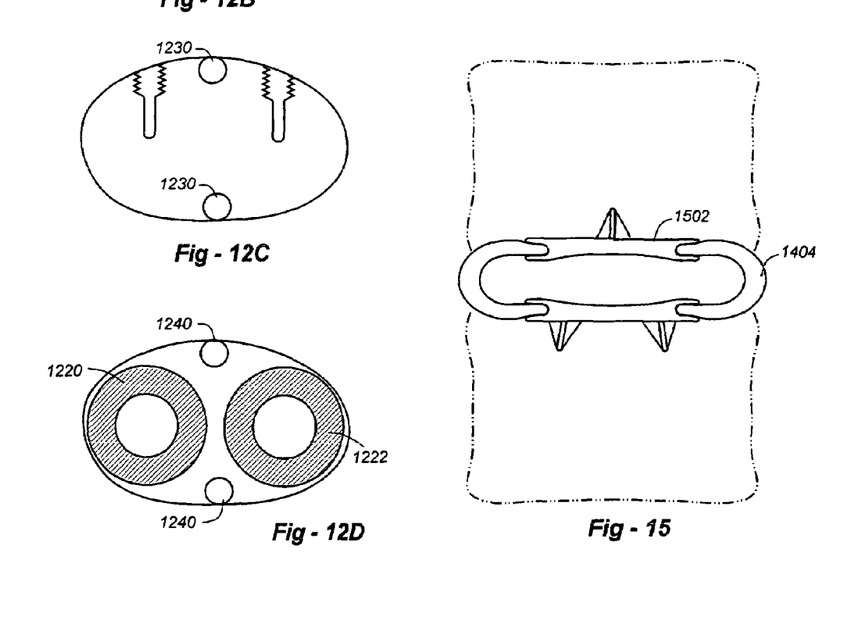
FIG. 12C is an axial cross section of the top tibial tray including circular pistons.
FIG. 12D is a view of the top of the bottom tibial tray.
FIG. 15 is a sagittal cross section of the anterior portion of the spine and an alternative embodiment of the ADR wherein the endplates have been eliminated.

FIG. 12A is a sagittal cross section of an embodiment of the device for cushioning the tibial component of a Total Knee Replacement (TKR). FIG. 12B is the view of the front of the tibial component drawn in FIG. 12A. Item 1202 represents the polyethylene tray which is seated in a metal tray 1204 including projections that piston in and out of a metal tray 1206 in the tibia. The cushioning elements 1220, 1222 are positioned between the two metal trays. The polyethylene component can be eliminated in embodiments of the device that have a metal articular surface. The trays and or the tire like component are porous to allow fluid movement in hydrogel-filled embodiments. FIG. 12C is an axial cross section of the top tibial tray. The circular pistons 1230 are also drawn. FIG. 12D is a view of the top of the bottom tibial tray including cylinders 1240 for the pistons.

Figure 13:
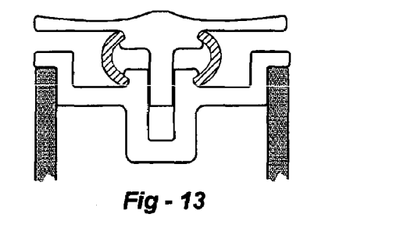
FIG. 13 is a sagittal cross section of an alternative embodiment including a metal articulating surface.

FIG. 13 is a sagittal cross section of an alternative embodiment of a TKR device including a metal articulating surface. A large portion of the cushioning element is positioned within the intramedullary canal of the tibia. The tibia is represented by the dotted area of the drawing. The embodiment of the device drawn eliminates the locking mechanism required with modular cushioning components. A single piston and cylinder are used in this embodiment of the device that mentions the option of using shape memory materials as a mechanism to lock the hub-like component to the projection from the ADR endplate.

Figure 14:
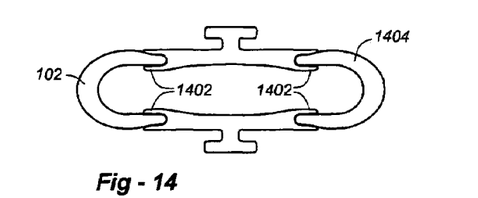
FIG. 14 is a sagittal cross section of an alternative cushion module.

FIG. 14 is a sagittal cross section of a cushion module similar to that drawn in FIG. 2, with the exception that the hydrogel sides of the hub-like components have raised rims 1402 that helps hold the tire like component 1404.

FIG. 15 is a sagittal cross section of the anterior portion of the spine and a different alternative embodiment of the ADR with the endplates eliminated. In this case, a tire-like component 1502 cooperates directly with the hub-like components 1504 and the vertebral endplates.

Figure 16A:
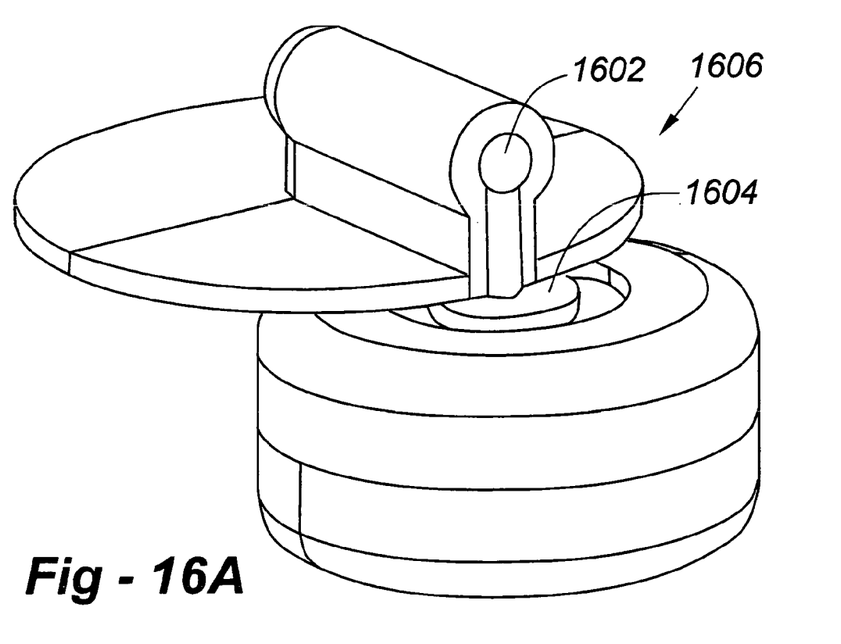
FIG. 16A is an oblique, lateral view of an embodiment including projection from the hub which are releaseably attached to a projection from the ADR endplate.

FIG. 16A is an oblique, lateral view of a preferred embodiment of the ADR. The projection 1602 from the hub 1604 is releaseably attached to a corresponding receptacle in the ADR endplate 1606. A screw (not shown) is used to lock the seated hub in place. The threads of the screw preferably deform slightly to prevent back-out. The ADR endplate 1606 is itself designed to slide into a previously milled vertebra.

The modular cushioning component can cooperate with a single ADR endplate as drawn. Alternatively, the cushioning component can be placed between ADR endplates placed on the vertebral endplates on either side of the disc space. The raised circular area in the central portion of the hub, below the lockable projection, is smaller than the hole in the tire-like component to highlight the raised portion of the hub. The raised portion of the hub rests against the ADR endplate. A recess is created between the widest portion of the hub, which is inside the tire-like component, and the ADR endplate. The recess is slightly taller than the thickness of the tire-like component. The cooperation between the hub and the ADR endplate protects the portion of the tire-like component, above the extension of the hub, from axial compression. The smooth surface of the cushion side of the ADR endplate and the space between the hub and the ADR endplate facilitate radial expansion of the tire-like component. The tire-like hoop expands in a radial direction secondary to the outward force transferred from the hydrogel within the tire-like hoop. The hydrogel applies outward force on the tire-like hoop secondary to axial forces on the spine.

Figure 16B:
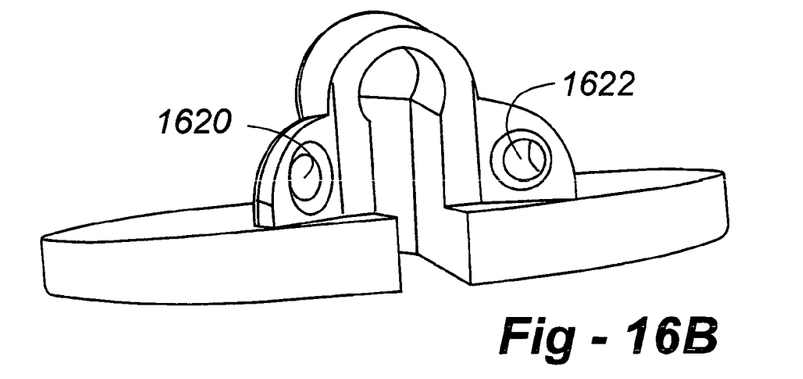
FIG. 16B is a view of the front of an alternative embodiment of the ADR endplate drawn in FIG. 16A.

FIG. 16B is a view of the front of an alternative embodiment of the ADR endplate drawn in FIG. 16A. Two diverging screws are placed through holes 1620, 1622 in the ADR endplate. The holes in the plate may include locking c-rings to prevent screw back-out. The screws are also recessed into the vertebrae to further decrease the risk of impingement of the screws on the soft tissues anterior to the spine.

Figure 16C:
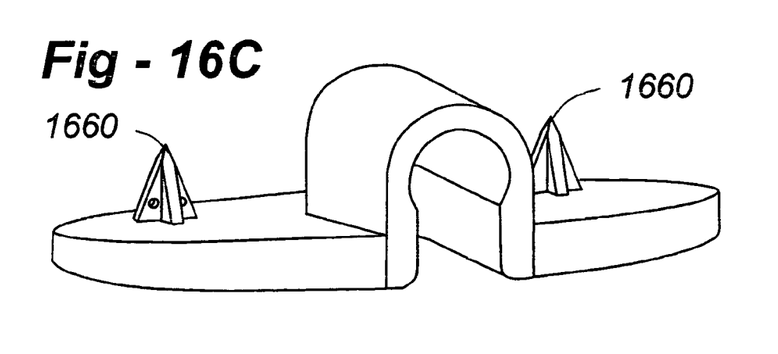
FIG. 16C is a view of the front of an alternative embodiment of the ADR endplate drawn in FIG. 16A.

FIG. 16C is a view of the front of an alternative embodiment of the ADR endplate drawn in FIG. 16A. The embodiment of the ADR endplate drawn in FIG. 16C is press fit into the vertebra from the disc space. The side walls of the portion of the ADR endplate tether mechanism are flush with top of the tether mechanism to allow insertion from the disc space. Spikes 1660 are use to resist extrusion of the ADR in an anterior or posterior direction. The tether mechanism prevents lateral movement of the ADR relative to the vertebrae. The tether and spikes cooperate to limit rotation of the ADR relative to the vertebrae.

Figure 17:
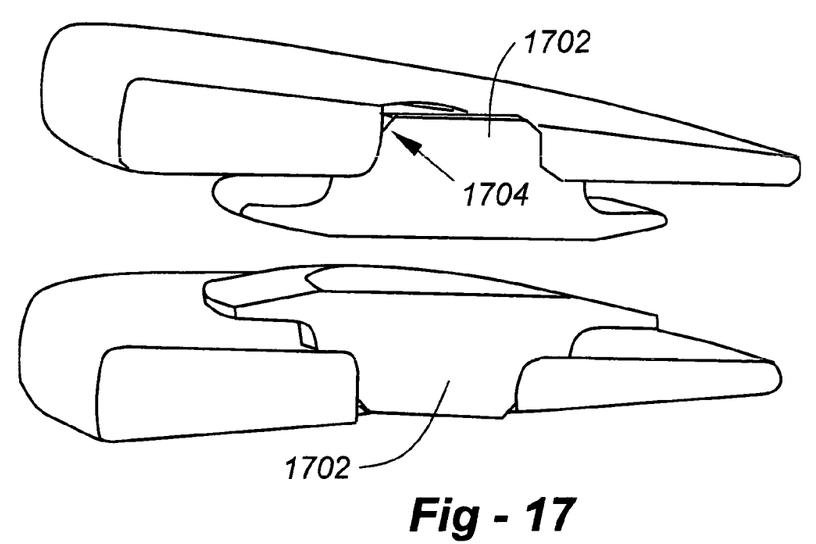
FIG. 17 is a sagittal cross section of the ADR with an alternative plate-hub locking mechanism. Projections from the hubs fit into holes in the ADR endplates.

FIG. 17 is a sagittal cross section of the ADR with an alternative plate-hub locking mechanism. In this embodiment, projections 1702 from the hubs fit into holes 1704 in the ADR endplates. The tire-like component was not drawn. Pressure from the hydrogel forces the projections from the hubs into the holes in the ADR endplates. The spikes on the vertebral side of the ADR endplates were not drawn. The recess between the widest portion of the hub and the ADR endplate is slightly wider than the thickness of the tire-like component.

Figure 18:
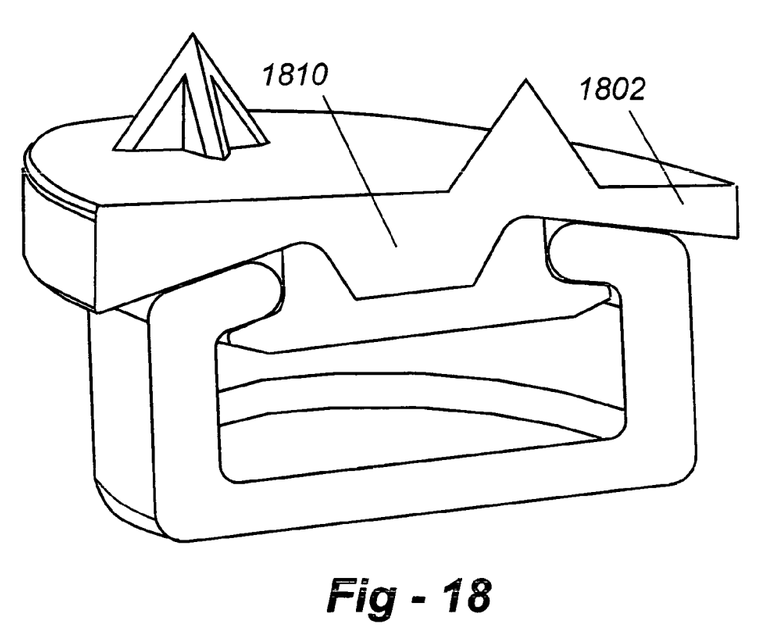
FIG. 18 is a sagittal cross section of another embodiment wherein a modular cushioning component is attached to a single ADR endplate.
Figure 19:
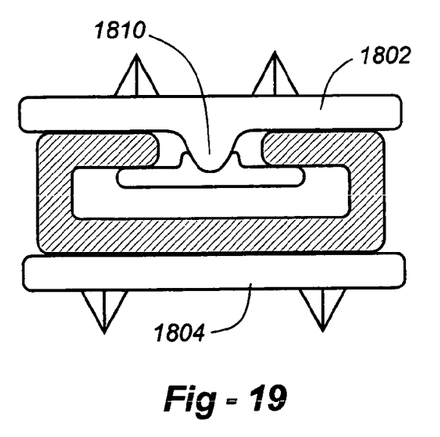
FIG. 19 is a sagittal cross section of an alternative embodiment of the ADR and a vertebra.

FIG. 18 is a sagittal cross section of another preferred embodiment of the ADR, wherein a modular cushioning component is attached to a single endplate 1802. The opposing side of the tire-like component cooperates directly with a vertebral endplate. The locking mechanism, similar to that drawn in FIG. 17, relies on a hydrogel, elastomer, or other appropriate filler material within the tire to exert force to the hub. A hole or recess in the center of the hub fits over a projection 1810 from the ADR endplate. The space between the hub and the ADR endplate is slightly larger than the thickness of the tire. FIG. 19 is a sagittal cross section of the embodiment of FIG. 18 showing the opposing endplate 1804.

Figure 20:
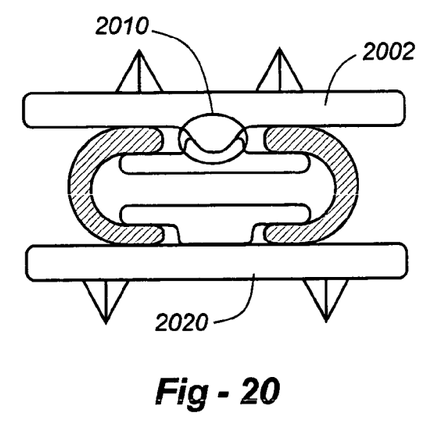
FIG. 20 is a sagittal cross section of another embodiment including one ADR endplate component tether and a second ADR endplate without the cushioning component tether.
Figure 21A:
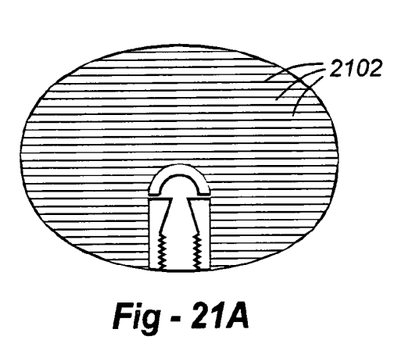
FIG. 21A is an axial cross section of the top of the alternative embodiment of FIG. 16A.
Figure 21B:
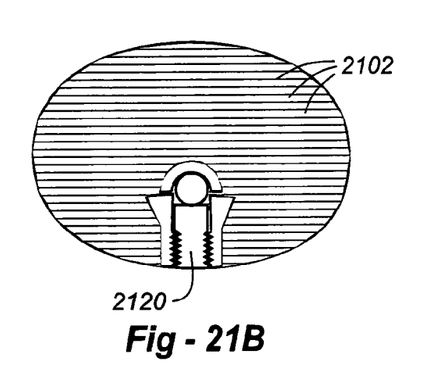
FIG. 21B is an axial cross section of the ADR drawn in FIG. 21A.

FIG. 20 is a sagittal cross section of yet another ADR embodiment wherein one endplate 2002 has a cushioning component tether 2010 and a second ADR endplate 2020 without the cushioning component tether. FIG. 21A is an axial cross section of the top of an alternative embodiment of the ADR drawn in FIG. 16A. FIG. 21B is an axial cross section of the ADR drawn in FIG. 21A. Deployable protrusions are incorporated into the sides of the ADR component to hold the projection from the hub. Ridges (horizontal lines 2102) increase the friction between the ADR endplate and the vertebrae. A locking screw 2120 deploys the protruding sidewalls of the portion of the ADR endplate that retains the projection from the hub.

Figures 22A, 22B, 23:
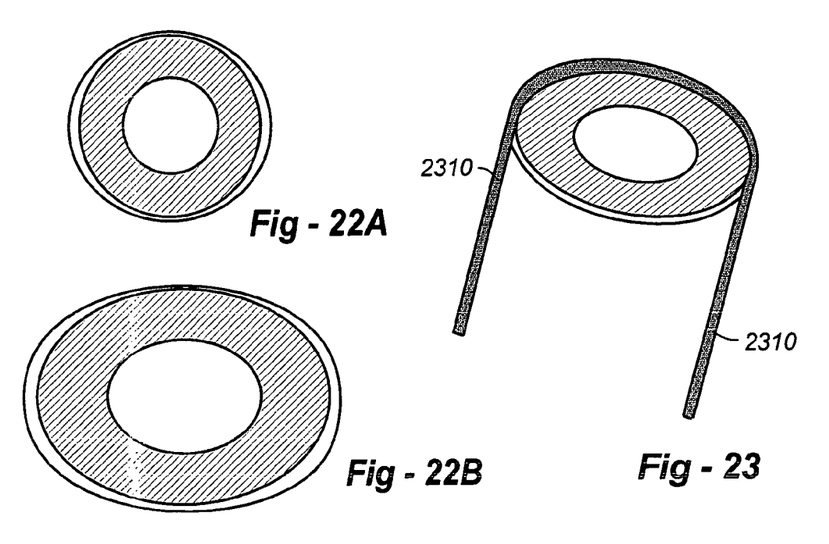
FIG. 22A is a top view of a circular, tire-like component and a circular ADR endplate.
FIG. 22B is a top view of an alternative, elliptically shaped ADR endplate component.
FIG. 23 is a top view of the device of FIG. 22C including a removable member placed around the modular cushion component prior to insertion.

FIG. 22A is a view of the top of a circular tire-like component and a circular ADR endplate. FIG. 22B is a view of the top of an alternative endplate which is elliptical in shape. FIG. 23 is a view of the top of the device drawn in FIG. 22C. A removable member 2310, such as a ribbon, is placed around the modular cushion component prior to inserting the modular cushion component into the disc space. This allows the surgeon to pull on the ribbon after insertion of the modular cushion component to assure the hub of the cushion component has seated on the projection from the ADR endplate. A properly seated cushion component should be difficult to pull out of the disc space. The ribbon is removed from behind the ADR by pulling on only one end of the ribbon.

Figure 24A:
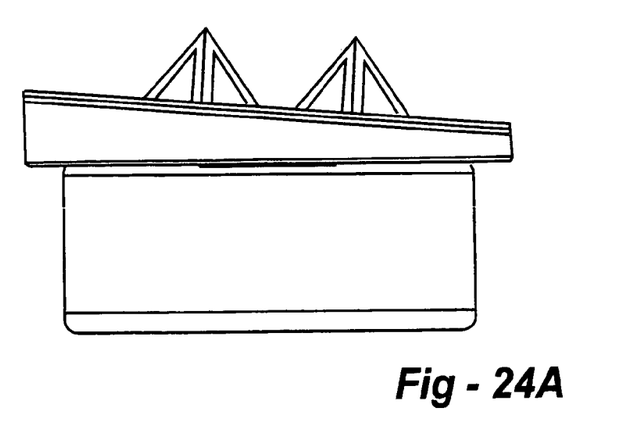
FIG. 24A is a top view of a wedge-shaped ADR endplate with strategically spaced endplate penetration spikes.
Figure 24B:
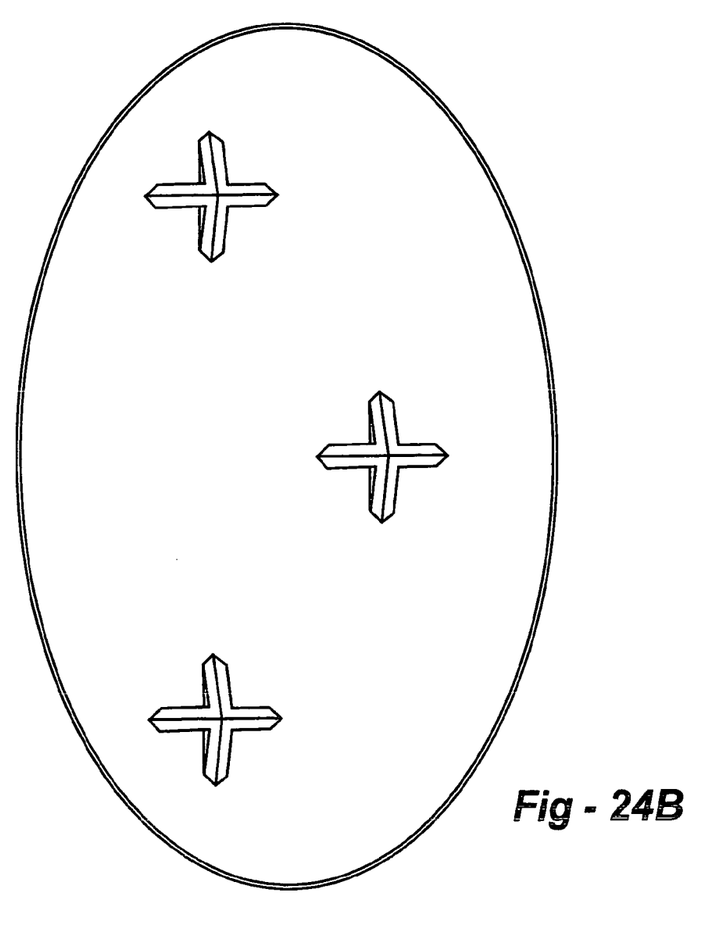
FIG. 24B is a side view of a wedge-shaped ADR endplate with strategically spaced endplate penetration spikes.

FIG. 24A is a top view and FIG. 24B side view of a wedge-shaped ADR endplate with strategically spaced endplate penetration spikes.

Figure 25A:
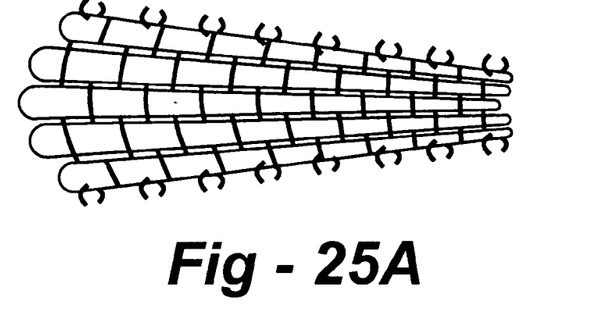
FIG. 25A is a view of the side of a hoop-mesh skeleton used in another embodiment of the ADR.
Figure 25B:
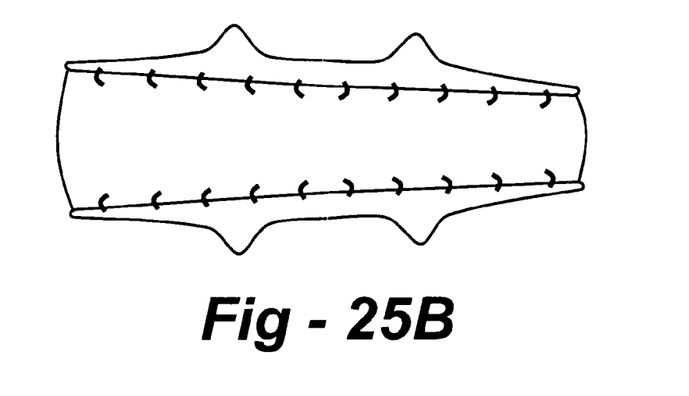
FIG. 25B is a view of the side of the ADR drawn in FIG. 25A, after its completion.
Figure 25C:
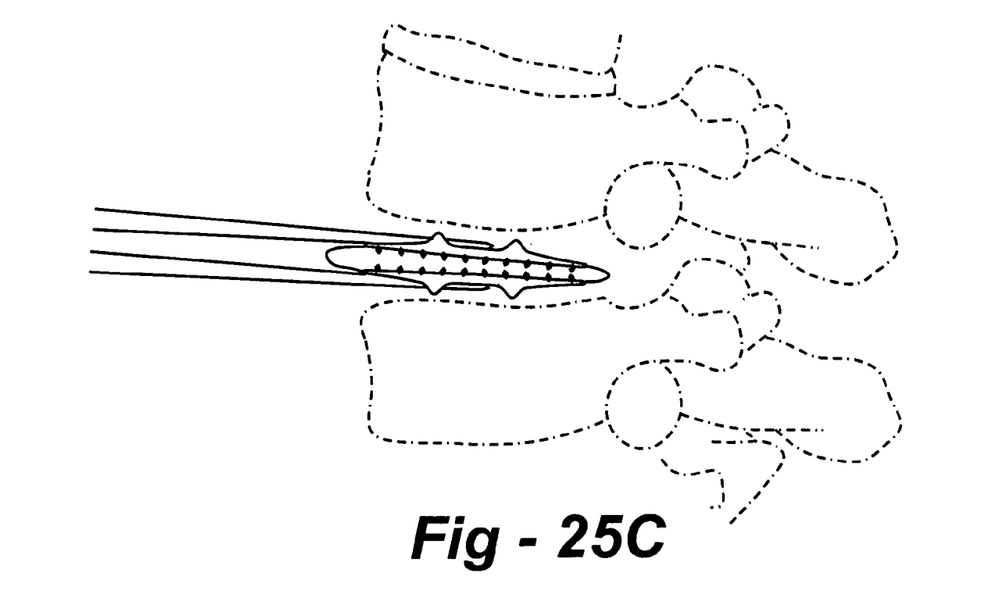
FIG. 25C is a view of the side of the spine and the ADR drawn in FIG. 25B.

The embodiment of the ADR drawn in FIG. 25A–C utilizes the bead construction of commercial tires. Hoops made of Nitinol, titanium, Kevlar, or other elastic materials are connected with perpendicular wires in a basket weave type arrangement. Conversely, the horizontal hoops could be connected by vertical hoops similar to the arrangement of the hoops in chain mail. The horizontal hoops could be somewhat taller anteriorly than posteriorly to fit the wedge shaped disc space. In any event, the finished hoop-mesh skeleton is taller anteriorly than posteriorly.

The hoop-mesh skeleton is covered with vulcanized elastomer much like the wire hoops within the bead of commercial tires are covered with vulcanized elastomer. Molds, liquid elastomers, and heat as used in the commercial tire industry could be used to surround the hoop-mesh skeleton with elastomers. Bias ply fibers could be incorporated into the elastomer.

The elastic horizontal hoops and vertical skeleton members resist radial expansion of the tire. The elastic horizontal hoops and vertical members expand and contract in reaction to forces applied by a hydrogel, gas, liquid, or other polymer within the center of the ADR.

The elastomer surrounding the hoop-mesh skeleton provides a smooth surface to cooperate with the hydrogel or other polymer center of the ARD. The elastomer also serves to prevent the extrusion of the hydrogel or other polymer from spaces between the hoops. Lastly, the elastomer assists the hoops in resisting radial expansion.

The completed carcass is flexible in a superior to inferior direction. The carcass may be more flexible anteriorly than posteriorly or at the sides of the carcass.

In the preferred embodiment, the carcass cooperates with an ADR endplate (EP) on its, superior and inferior surfaces, to contain a hydrogel core. The carcass is connected to the perimeter of the ADR EPs. Wire rings could connect the carcass to holes in the ADR EPs. The wire rings could be laser welded after connecting the two components. Alternatively, the carcass could be stretched over the perimeter of the ADR EPs much like a tire stretches over the hub of a wheel. A band could be tightened over the portion of the tire that lies over the ADR EPs.

Fluid could move into the hydrogel through holes in the ADR EPs, the elastomer, or the space between the tire and the ADR EPs.

The ADR could be compressed prior to its insertion in the disc space. The arms of the tool that compress the ADR would also help make the spikes from the ADR EP less prominent, thus reducing the risk of soft tissue injury during the insertion process. The partially hydrated hydrogel imbibes additional fluid after insertion of the ADR to further improve the ADR press fit.

FIG. 25A is a view of the side of a hoop-mesh skeleton used in another embodiment of the ADR. Horizontal hoops made of an elastic material, are connected by vertical members. The open rings at the top and bottom of the skeleton are used to connect the elastic skeleton to the ADR endplates.

FIG. 25B is a view of the side of the ADR drawn in FIG. 25A, after its completion. The skeleton has been embedded in an elastomeric material. Rings connect the elastomerized skeleton to two ADR endplates. The rings connecting the two components have been closed and laser welded.

FIG. 25C is a view of the side of the spine and the ADR drawn in FIG. 25B. A clamp like tool is used to compress the ADR. The tool is removed after inserting the compressed ADR into the disc space.

This invention offers numerous advantages over existing designs. As opposed to all metal or metal/polyethylene designs, the cushioning components disclosed herein behave more like a natural disc while protecting adjacent discs (transfers less force to the adjacent discs). The modular cushion components and other design elements allow replacement of the cushion component without revising well fixed ADR EPs. The modular designs also reduce implant inventory and allow insertion of ADR EP or EPs first. Inserting the ADR EPs separately allows longer spikes or projections that are press fit into the vertebrae EP.

Indeed, certain embodiments allow replacement of the cushioning component without removing one or both of the ADR endplates. The use of polyethylene provides minimal cushioning, since the components are shaped to articulate with metal components to permit spinal motion. The modular cushion components disclosed herein permit spinal motion through compression of the modular cushion component rather than articulation as seen in the above mentioned patents.

The use of a hybrid design (ADR EP attached to superior vertebra and tire-like component) acts directly on the superior EP of the inferior vertebra. The ADR EP fits over a milled or shaped surface of the superior vertebra. The inferior EPs of vertebrae are generally less flat than the superior EPs of vertebrae. The shapes of the inferior EPs are also more variable than the shapes of the superior EPs. Extensive experience with Total Knee Replacement over the last few decades suggest it is better to prepare a reproducible flat surface on the tibia than to manufacture a wide variety of tibia component shapes to fit the various shapes of the tibia articular surface. Similar to TKRs, the hybrid ADR attaches a flat ADR EP onto the cut surface of the superior vertebrae.

Disc space is limited in size, and experience with TKRs suggests thin polyethylene components leads to early failure. By eliminating one of the ADR endplates, the modular cushioning component of the disclosed hybrid ADR can be thicker. The modular cushion components disclosed herein can conform to the EP of the inferior vertebra. Furthermore, the durability of tire-like components give the cushion component excellent wear characteristics, even with direct placement of the cushion component onto the EP of the vertebra. The smooth surface of our tire like component should minimize wear on the vertebra EP. Certain design are unique in that they use a single ADR EP. It is also the only ADR design that attaches a cushion component to a single ADR endplate.

The coupling mechanisms between the ADR EP and the modular cushion component prevent the cushion component from extruding from the disc space. The coupling mechanism also keeps the cushion component centered in the disc space. Eccentric placement of free compressible components or NR ADRs increases the probability of extrusion of the component or ADR. The coupling mechanisms also enable the insertion of a component between the ADR EPs that is wedge shaped and thickest in the front of the component. The disc in the cervical and lumbar spines are naturally thickest at their anterior most portion.

The Hybrid design is the only known ADR to couple the components using a reversibly deformable cushion component that cooperates with a metal projection from the ADR EP. The Hybrid design, as well as a few of the other embodiments, do not require precise alignment between ADR EPs placed over both vertebral EPs. Other modular ADRs place polyethylene between two metal ADR EPs. The ADR EPs must align perfectly for the polyethylene insert to articulate properly with the ADR EPs.

The various materials prescribed herein are biocompatible and approved for use in humans. These include hydrogels, elastomers, and metals such as titanium. The hydrogels are able to change their fluid content, and thus size, as pressure on the hydrogel is applied. The migration of fluid to and from the disc space may improve the nutrition of the living cells within the disc. The hydrogel embodiments are also capable of increasing in size by imbibing fluid after they are inserted. Thus, hydrogels can grow to "custom fit" the available disc space. Dehydrated hydrogels can be inserted through smaller openings in the ADR or disc space. Hydrated hydrogels grow to fit the available space after insertion.

In certain embodiments, hydrogel is contained within an elastomeric hoop called a tire. The preferred hydrogel has high water content to function like the NP of the natural disc. In particular, axial loads on the hydrogel are converted into radial forces on the tire. The tire expands in a radial direction due to the loads transferred by the hydrogel, and resists the loads via hoop stresses. The "tire" also limits the amount of hydrogel shape change (the hydrogel wants to decrease in height and increase in width and length with axial load).

The preferred high water content hydrogel is mucous like in consistency, acting similar to hydraulic fluid which transfers load to the tire. In contrast, the hydrogels of prior-art devices are firmer, to act as the primary load bearing member In our device, axial compression of the disk space is transformed into radial distension of the tire and enlargement of the cross sectional area. Because area grows as the square of the radius, an increment of axial deflection produces a smaller increment of radial deflection.

The tire designs also act as a spring to restore the disk space as the load is decreased. The tire dampens most of the forces on the spine. The hydrogel, for the most part, transfers forces to the hoop. These devices rely on the hydrogel and the tire to share the dampening forces, with the tire doing bulk of the dampening. The tire may contain cloth-like material and elastomers.

A preferred embodiment is elliptical in shape to maximize the amount of cushioning material in the disc space. Circular shaped ADRs may leave precious disc space unoccupied. According to this invention, a single ADR device is inserted, since paired ADRs may risk extrusion. If one of the paired ADR maintains the disc height, the lack of axial load and thus friction on the other paired ADR can lead to extrusion of the unloaded ADR.

The use of a "hub" has several important features. For one, the hub cooperates with the ADR EP to create a space for the top of the tire that is slightly wider than the thickness of the hub. The space protects the portion of the tire between the hub and the ADR EP from axial compression. Sparing the tire from axial compression facilitates radial expansion of the hub during axial compression of the ADR. The smooth surface of the hub and the ADR EP further promotes expansion of the tire with axial compression. Protecting a portion of the tire from axial compression may prolong the life of the tire.

The tire also stretches to allow hub insertion through a hole in the hoop that is smaller than the hub. The tire returns to its original shape after the hub is inserted. Inelastic bags would not have the elastic properties of our tire.

One embodiment of the tire has a hole in the top; another has holes in the top and bottom of the tire. The hub cooperates with the tire to trap the hydrogel in the tire. The overlap between hub and the tire permit the hole in the tire to enlarge (with radial expansion) yet hold the hydrogel in place.

The use of a variable center of rotation, as opposed to a fixed center of rotation, also function more like natural disc by restoring normal disc kinematics. This allows all normal disc motions (direction and magnitude) including flexion, extension, lateral bending, translocation, and rotation. The various ADR designs maintain distraction to decrease the pressure on compressed nerves and to decrease the pressure on the facet joints.

ADR endplates with holes for insertion of a distraction instrument is believed to be unique. Among other advantages, this allows distraction instruments to hold the disc space in a distracted position while the modular cushion component is inserted. The use of a 'ribbon' to test proper coupling of the modular components, and the resistance to extrusion of the ADR, is also thought to be unique.

Other novel disclosures include the use of screws recessed into the body of the vertebra. Recessed screws minimize the risk of the screws backing out into the aorta. The ADR plates may also include a mechanism, similar to those used in plates for the cervical spine, to prevent screw back-out. The use of a keel with an enlargement in the portion above the endplate of the vertebra is also believed to be unique. The enlargement in the keyhole-like slot resists forces trying to pull the ADR EP from the vertebra. Another unique feature is the use of deployable projections into the vertebrae to resist extrusion of ADRs, as is the use of perpendicular projections from the surface of the ADR EP.

We claim:

1. A modular implant configured for placement between opposing bone surfaces, comprising:
   a pair of opposing endplate components, each attached to one of the opposing bone surfaces;
   a cushioning component having an outer, compressible structure with crossing overlapping fibers attached to a central hub; and
   mechanism associated with the central hub for interlocking the cushioning component to one or both of the endplates.

2. The implant of claim 1, wherein the cushioning component includes a filler material.

3. The implant of claim 2, wherein the filler material is a gas, liquid, foam, gel or hydrogel.

4. The implant of claim 2, wherein one or both of the endplate components include a modified surface to increase adherence to respective bone surfaces.

5. The implant of claim 4, wherein the modified surface includes spikes or other projections.

6. The implant of claim 4, wherein the modified surface is conducive to bony ingrowth.

7. The implant of claim 1, wherein the mechanism for interlocking the cushioning component to one or both of the endplates includes a projection on the central hub and a corresponding groove on the endplate allowing the implant to be pushed into position.

8. The implant of claim 7, further including a screw or other fastener for maintaining the projection in the groove.

9. The implant of claim 1, further including a clip or other device for compressing the implant until insertion between the opposing bone surfaces.

10. The implant of claim 1, wherein the endplates are configured for adherence to vertebral endplates.

11. The implant of claim 1, wherein:
   one of the endplates is configured for adherence to a prepared distal femur; and
   the other of the endplates is configured for adherence to a prepared proximal tibia.

* * * * *